United States Patent [19]
Jarreau et al.

[11] Patent Number: 4,578,382

[45] Date of Patent: Mar. 25, 1986

[54] 4-ACYLAMINO-1-AZAADAMANTANES, AND COMPOSITIONS FOR USE THEREOF IN MEDICINE

[75] Inventors: Francois X. Jarreau, Versailles; Jean-Jacques Koenig, Vernou la Celle sur Seine, both of France

[73] Assignee: Etablissements Nativelle S.A., France

[21] Appl. No.: 427,343

[22] Filed: Sep. 29, 1982

[30] Foreign Application Priority Data

Oct. 5, 1981 [FR] France .................... 81 18682

[51] Int. Cl.⁴ .................. A61K 31/435; C07D 471/18
[52] U.S. Cl. ........................................ 514/245; 546/72
[58] Field of Search ................ 546/72, 97; 424/256; 514/245

[56] References Cited

U.S. PATENT DOCUMENTS

| | | | |
|---|---|---|---|
| 3,493,577 | 2/1970 | Gagneaux | 546/97 |
| 3,502,684 | 3/1970 | Gagneaux | 546/97 |
| 4,093,734 | 6/1978 | Kruger et al. | 546/133 |

FOREIGN PATENT DOCUMENTS

| | | | |
|---|---|---|---|
| 769615 | 11/1971 | Belgium | 546/133 |
| 2358404 | 2/1978 | France . | |
| 0076755 | 4/1983 | France | 546/97 |

*Primary Examiner*—Glennon H. Hollrah
*Assistant Examiner*—D. B. Springer
*Attorney, Agent, or Firm*—Sughrue, Mion, Zinn, Macpeak and Seas

[57] ABSTRACT

The invention relates to 4-acylamino-1-azaadamantanes represented by general formula (I):

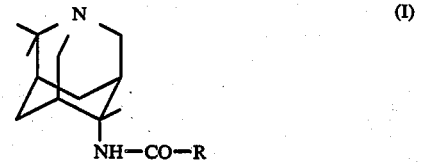

wherein R represents an alkyl group, a substituted alkyl group, an aryl group or a substituted aryl group, useful in particular, for the treatment of cardiovascular diseases.

10 Claims, No Drawings

4-ACYLAMINO-1-AZAADAMANTANES, AND COMPOSITIONS FOR USE THEREOF IN MEDICINE

FIELD OF THE INVENTION

The present invention relates to new adamantane derivatives, and more particularly to derivatives of the 4-acylamino-1-azaadamantane series, the use thereof in medicine and a process for the preparation thereof.

BACKGROUND OF THE INVENTION

Various compounds are known which comprise in their molecule a nucleus of the adamantyl type, whose structure with four condensed hexagonal rings produces various particular physical and chemical properties due to its steric rigidity. Derivatives of the azaadamantane or [3,3,1]azatricyclodecane types, with an adamantyl group wherein a nitrogen atom is substituted for a bridgehead carbon atom, at the junction of three of the condensed rings of the tetracyclic adamantyl nucleus, have been studied very little. An example of a method of preparation of such derivatives of the azaadamantane type is described in French Pat. No. 2,358,404.

SUMMARY OF THE INVENTION

An object of the invention is new 4-acylamino-4,8,8-trimethyl-1-azaadamantanes useful in medicine for the treatment of cardiovascular diseases.

An object of the invention is also a process for the preparation of new derivatives of the 4-acylamino-4,8,8-trimethyl-1-azaadamantane type.

A further object of the invention is new medications composed of the derivatives of the 4-acylamino-4,8,8-trimethyl-1-azaadamantane type, as well as pharmaceutical compositions containing the same, for the treatment of cardiovascular diseases.

The new 4-acylamino-1-azaadamantanes of the present invention can be represented by general formula (I) below:

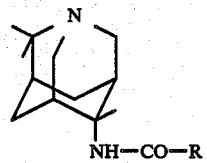

(I)

wherein R represents an alkyl group, a substituted alkyl group, an aryl group, or a substituted aryl group.

DETAILED DESCRIPTION OF THE INVENTION

The alkyl group represented by R in formula (I) above can be a lower alkyl group with 1 to 4 carbon atoms such as a methyl, ethyl, n-propyl, isopropyl, butyl group, etc.; this alkyl group can be substituted, in particular by an amino, alkoxy or cyano group, to form, for example, a 2-aminoethyl or dimethylaminomethyl group, etc.

When R represents an aryl group, this group can in particular be a phenyl group, a naphthyl group, a tolyl group, a phenethyl group, a benzyl group, a phenylpropyl group, a 2,2-diphenyl ethyl group or a 3,3-diphenylpropyl group.

The aryl group represented by R may bear one or more substituents selected from among a halogen atom or an alkyl (for example, methyl, ethyl, propyl, butyl, etc.), hydroxy, methylenedioxy, alkoxy (for example methoxy, ethoxy, isopropoxy, etc,), amino, alkylamino (for example, isopropylamino), dialkylamino (for example, dimethylamino, diethylamino, etc.), nitro, cyano, acylamino (for example, acetylamino), acyl (for example, formyl, acetyl, etc.), or haloalkyl (for example, trifluoromethyl, trichloromethyl, etc.) group, to form, for example, a p-nitrophenyl, p-aminophenyl, p-acetylaminophenyl, p-methoxyphenyl, p-methoxyphenethyl, 3,4-dimethoxyphenyl, 3,4-dimethoxyphenethyl, 3,4-dimethoxybenzyl, 3,4-dihydroxyphenyl, p-chlorophenyl, 3,4-dichlorobenzyl, 3,4-methylenedioxyphenyl, 3,4-methylenedioxybenzyl, p-trichloromethylphenyl, p-trifluoromethylbenzyl, p-cyanophenyl, p-cyanophenethyl, 2-cyano-2,2-diphenylethyl, 3-cyano-3,3-diphenylpropyl, group etc.

The invention preferably relates to compounds of general formula (I) wherein R represents an aryl group such as a phenyl, benzyl, phenethyl, phenylpropyl, 2,2-diphenyl ethyl and 3,3-diphenyl propyl group, or a substituted aryl group such as a p-nitrophenyl, p-aminophenyl, p-acetylaminophenyl, p-methoxyphenyl, 3,4-dimethoxyphenyl, 3,4-dimethoxybenzyl, p-methoxybenzyl, p-methoxyphenethyl and 3,4-methylenedioxy phenyl group.

The invention also relates to the salts of derivatives of the 4-acylamino-1-azaadamantane type, represented by general formula (I) above, and in particular to the pharmaceutically acceptable salts, obtained by reacting a mineral or organic acid with the derivative of formula (I) as a base. This salt forming reaction can be carried out using methods which are conventional in the art, by reacting the acid and the derivative of the 4-acylamino-1-azaadamantane type of formula (I) in substantially stoichiometric proportions, in an appropriate solvent such as methanol, ethanol, isopropanol, tetrahydrofuran, dioxane, methylene chloride, diethyl ether, ethyl acetate, etc. The acid can, for example, be hydrochloric acid, lactic acid, tartaric acid, phosphoric acid, oxalic acid, formic acid, sulfuric acid, maleic acid, hydrobromic acid, hydriodic acid, etc.

The new 4-acylamino-4,8,8-trimethyl-1-azaadamantanes of the invention can be obtained from the 4-amino-4,8,8-trimethyl-1-azaadamantane of general formula (II) below:

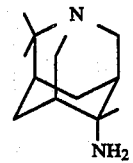

(II)

by action of an acylation agent, in an appropriate solvent.

The acylation reaction can be carried out using conventional techniques, for example, by means of an acid, an acid chloride, an ester or an anhydride. In particular an acylation agent can be selected from acetic anhydride, propionic anhydride, N-diethylaminoacetic (or diethylglycine) acid, N-dimethylaminoacetic acid, benzoyl chloride, p-nitrobenzoic acid chloride, p-methoxybenzoic acid chloride, phenylacetic acid, 3-phenyl propionic acid, 3,3-diphenyl propionic acid, phenylbutyric acid, etc. The acylation agent is preferably used in slight excess.

All the solvents currently used in acylation reactions are suitable for the preparation of the derivatives of the invention, in particular an ether such as diethyl ether, tetrahydrofuran, dioxane, a chlorinated solvent such as carbon tetrachloride, chloroform, methylene chloride, or an ester such as ethyl acetate. In accordance with the invention, methylene chloride and chloroform are preferably used.

The acylation reaction of 4-amino-4,8,8-trimethyl-1-azaadamantane of formula (II) is carried out cold, and it may be advantageous to dissolve the starting materials in a solvent cooled on an ice bath or on a cold water bath and to allow the temperature to increase slowly during the reaction.

So as to facilitate the acylation reaction, in particular when the acylation agent is an acid such as phenylacetic acid, phenylbutyric acid, etc., it is advantageous to add N-hydroxysuccinimide and dicyclohexylcarbodiimide to the reactive medium. The quantities used can, for example, be on the order of 1 to 2 moles of N-hydroxysuccinimide and 1 to 3 moles of dicyclohexylcarbodiimide for 1 to 2 moles of acid and 1 mole of 4-amino-4,8,8-trimethyl-1-azaadamantane of formula (II).

As necessary, the base obtained may be converted to the salt, as indicated above, or transformed by modification of a substituent. For example, the derivative of formula (I), where R is a p-nitrobenzyl group, obtained by action of p-nitrobenzoic acid chloride on the derivative of formula (II), can be reduced by hydrogenation with a catalyst to transform it into the corresponding derivative where R is a p-aminobenzoyl group which itself can be acetylated to form a p-acetylaminobenzoyl group using conventional techniques, for example, by action of acetyl chloride in tetrahydrofuran.

The 4-amino-4,8,8-trimethyl-1-azaadamantane of general formula (II) is a known product, described in French Pat. No. 2,358,404, which can be prepared from a pinene treated with a mercuric salt and a nitrile in an anhydrous medium in order to obtain a bicyclic imine which is reduced to an amine, then cyclized by the action of an aldehyde to yield the azaadamantane of formula (II).

The examples given below illustrate the invention in greater detail, without limiting the scope thereof.

EXAMPLE 1

4-N-Propionylamino-4,8,8-trimethyl-1-azaadamantane 5 ml of propionic anhydride were added to a solution of 7 g of 4-amino-4,8,8-trimethyl-1-azaadamantane in 50 ml of methylene chloride, placed in a flask on an ice bath, while maintaining the mixture under agitation.

When the reaction was completed, 50 ml of water containing 5 ml of sodium hydroxide solution was poured therein, then decanted and washed with water. This was extracted with methylene chloride, washed, dried and the organic phases were distilled to obtain 9.2 g of a reddish oily residue which, after crystallization in a mixture of ethyl acetate and isopropyl ether, yielded 5.2 g of 4-N-propionylamino-4,8,8-trimethyl-1-azaadamantane (yield 60%).

Melting point = 110°-112° C. (ethyl acetate/isopropyl ether).

I.R. Spectrum (Nujol): $\nu = 3000$ to 3400 (3300,3050), 1630, 1540 cm$^{-1}$.

N.M.R. Spectrum (CDCl$_3$): $\delta = 1.11$ (3H, t, J=8), 1.27 (6H, s), 1.52 (3H, s), 1 to 1.4 (1H), 1.6 to 2.3 (6H), 2.15 (2H, Q, J=8), 2.98 (2H, d, J=14), 3.42 (2H, d, J=14), 5.53 (1H mobile) ppm.

T.L.C. (Thin layer chromatography).
(CH$_2$Cl$_2$/MeOH/NH$_4$OH: 84/16/3) RF=0.5.

The above product (5 g) was dissolved in 40 ml of heated tetrahydrofuran, and to this solution was added a solution of 20 ml of tetrahydrofuran containing 2.3 g of maleic acid. After filtration and washing with isopropyl ether, 7.2 g of 4-N-propionylamino-4,8,8-trimethyl-1-azaadamantane maleate was collected.

Melting Point = 190°-192° C. (tetrahydrofuran).

EXAMPLE 2

N-(diethylaminoacetyl)-4-amino-4,8,8-trimethyl-1-azaadamantane 10 g of diethylglycine hydrochloride was dissolved in 70 ml of methanol to which 5 g of sodium bicarbonate was added. The mixture was maintained under agitation for 2 hours, evaporated until dry, dissolved in methylene chloride and, after filtration, washing and evaporation of the solvent, 7.9 g of diethylglycine in the base form was obtained.

7 g of 4-amino-4,8,8-trimethyl-1-azaadamantane was reacted with the 7.9 g of diethylglycine obtained as indicated above, in the presence of 7.4 g of N-hydroxy succinimide and 15.4 g of dicyclohexylcarbodiimide, in 120 ml of methylene chloride, for 48 hours.

7.9 g (yield 72%) of N-(diethylaminoacetyl)-4-amino-4,8,8-trimethyl-1-azaadamantane was obtained which was purified by conversion to the dihydrochloride, then by crystallization in ethanol. The product was in the form of a colorless oil.

TLC (CH$_2$Cl$_2$/MeOH/NH$_4$OH: 85/15/2) Rf=0.5.

I.R. Spectrum (film): $\nu = 3000$ to 3600 (3320), 1670, 1510 cm$^{-1}$.

N.M.R. Spectrum (CDCl$_3$): $\delta = 1.05$ (6H, t, J=7), 1.30 (6H, s), 1.56 (3H, s), 1.0 to 2.3 (7H), 2.60 (4H, q, J=7), 2.98 (2H, s), 3.08 (2H, d, J=15), 3.55 (2H, d, J=15), 7.50 (1H mobile) ppm.

EXAMPLE 3

N-(p-aminobenzoyl)-4-amino-4,8,8-trimethyl-1-azaadamantane 6.8 g of 4-amino-4,8,8-trimethyl 1-azaadamantane was dissolved in 100 ml of chloroform, by cooling the solution on an ice bath, and 7.3 g of p-nitrobenzoic acid chloride dissolved in 70 ml of chloroform was added dropwise.

After reaction, the precipitate formed was collected by filtration and dissolved in ammonia. The aqueous phase was extracted with methylene chloride to yield 5.5 g of N-(p-nitrobenzoyl)-4-amino-4,8,8-trimethyl-1-azaadamantane, in the form of white crystals with a melting point of 206° C.

I.R. Spectrum (Nujol): $\nu = 3420$, 3200, 1650, 1600, 1570, 1520 cm$^{-1}$.

TLC (CH$_2$Cl$_2$, MeOH, NH$_4$OH, 80-20-1): Rf=0.60.

By reduction of the above product with hydrogen in the presence of platinum in a 10% methanol solution, followed by filtration and recrystallization in isopropanol, N-(p-aminobenzoyl)-4-amino-4,8,8-trimethyl-1-azaadamantane was obtained in the form of white crystals.

Melting Point: 218° C.

I.R. Spectrum (Nujol): $\nu = 3440$, 3320, 1640, 1610 cm$^{-1}$.

TLC (CH$_2$Cl$_2$-MeOH-NH$_4$OH, 80-20-1) Rf=0.40.

If desired, the above product can be acetylated by dissolving it in tetrahydrofuran, and dropwise adding a solution of acetyl chloride in tetrahydrofuran; after recrystallization in ethanol, N-(p-acetylaminobenzoyl)-4-amino-4,8,8-trimethyl-1-azaadamantane was obtained in the hydrochloride form.

Hydrochloride: Melting Point: 230° C. (ethanol).

I.R. Spectrum (Nujol): $\nu$=3650 to 2000, 1670, 1630, 1610, 1600, 1530, 1510 cm$^{-1}$.

Base: I.R. Spectrum (Nujol): $\nu$=3600 to 2000, 1670, 1640, 1600, 1535, 1505 cm$^{-1}$.

T.L.C. (AcOEt+20% HNEt$_2$) Rf=0.20.

EXAMPLE 4

N-(3-phenylpropionyl)-4-amino-4,8,8-trimethyl-1-azaadamantane 15.6 g of 3-phenylpropionic acid was reacted on 12.5 g of 4-amino-4,8,8-trimethyl-1-azaadamantane in the presence of 8.2 g of N-hydroxysuccinimide and 24.0 g of dicyclohexylcarbodiimide in 130 ml of methylene chloride for 72 hours.

After filtration, treatment and separation of the dicyclohexylurea formed, purification by conventional techniques and crystallization in ethyl acetate, 13.7 g of N-(3-phenylpropionyl)-4-amino-4,8,8-trimethyl-1-azaadamantane was obtained (yield 65%).

Melting point: 134°–136° C. (ethyl acetate).

I.R. Spectrum (Nujol): $\nu$=2800 to 3500 (3230 and 3050), 1645, 1600, 1565, 1490, 755 and 700 cm$^{-1}$.

NMR Spectrum (CDCl$_3$): $\delta$=1.25 (6H, s), 1.49 (3H, s), 1.0 to 2.3 (7H), 2.5 (2H, m), 2.9 (2H, m), 3.0 (2H, d, J=15), 3.45 (2H, d, J=15), 5.35 (1H mobile), 7.35 (5H) ppm.

TLC (CH$_2$Cl$_2$/MeOH/NH$_4$OH 84/16/3): Rf=0.55.

4.5 g of the above base was dissolved in 30 ml of tetrahydrofuran, the viscous precipitate was decanted, dissolved in 15 ml of absolute ethanol and the solution was poured into 100 ml of isopropyl ether under agitation on an ice bath. After filtration, 5.9 g of N-azaadamantyl-phenylpropionamide tartrate was obtained (yield 89%).

Melting Point: 95°–110° C. (viscous melting) (ethanol/isopropyl ether).

EXAMPLE 5

N-[3-(p-methoxy-phenyl)propionyl]-4-amino-4,8,8-trimethyl-1-azaadamantane 8.4 g of 3-p-methoxyphenylpropionic acid was reacted with 6.0 g of 4-amino-4,8,8-trimethyl-1-azaadamantane, in the presence of 4.3 g of N-hydroxysuccinimide and 13.6 g of dicyclohexylcarbodiimide, in 80 ml of methylene chloride for 40 hours.

The basic fraction was extracted using conventional techniques and the residue was crystallized in ethyl acetate. In this manner 5.6 g of N-[3-(p-methoxyphenyl)propionyl]-4-amino-4,8,8-trimethyl-1-azaadamantane was obtained with a yield of 51%.

Melting Point: 149°–151° C. (ethyl acetate).

T.L.C. (CH$_2$Cl$_2$/MeOH/NH$_4$OH 85/15/2) Rf=0.55.

I.R. Spectrum (Nujol): $\nu$=3000 to 3600 (maximum about 3290), 1635, 1610, 1550, 1510 cm$^{-1}$.

N.M.R. Spectrum (CDCl$_3$): $\delta$=1.23 (6H, s), 1.48 (3H, s), 1.0 to 2.3 (7H), 2.50 (2H, m), 2.90 (2H, m), 2.98 (2H, d, J=15), 3.45 (2H, d, J=15), 3.75 (3H, s), 5.60 (1H mobile), 6.77 (2H, d, J=9), 7.13 (2H, d, J=9) ppm.

The above base was transformed into the corresponding hydrochloride by conventional techniques, by the action of concentrated hydrochloric acid in ethanol.

Melting Point: >260° C. (ethanol).

EXAMPLE 6

N-(3,3-diphenylpropionyl)-4-amino-4,8,8-trimethyl-1-azaadamantane 8.4 g of 3,3-diphenylpropionic acid in two fractions of 6.4 g and 2 g were reacted on 4.5 g of 4-amino-4,8,8-trimethyl-1-azaadamantane in the presence of 3.3 g of N-hydroxy succinimide and 9.5 g of dicyclohexylcarbodiimide in 75 ml of methylene chloride for 48 hours. After treatment and elimination of the dicyclohexylurea formed, using conventional techniques, 6.4 g of a crystalline residue was obtained, which was purified by crystallization in a mixture of ethyl acetate and ethanol.

Melting Point: 222°–224° C. (ethanol/ethyl acetate).

I.R. Spectrum (Nujol): $\nu$=3285, 1660, 1635, 1595, 1550, 1540, 700 and 690 cm$^{-1}$.

N.M.R. Spectrum (CDCl$_3$): $\delta$=1.23 (6H, s), 1.38 (3H, s), 0.9 to 2.3 (7H), 2.90 (2H, d, J=8), 2.93 (2H, d, J=15), 3.35 (2H, d, J=15), 4.50 (1H, t, J=8), 5.35 (1H mobile), 7.20 (10H, s) ppm.

T.L.C. (CH$_2$Cl$_2$/MeOH/NH$_4$OH 85/15/2) Rf=0.4

6.4 g of the crude base obtained as indicated above were dissolved in 100 ml of boiling tetrahydrofuran. 2.5 g of L(+)tartaric acid dissolved in 25 ml of hot tetrahydrofuran was added. This was left to cool, filtered and the precipitate obtained (8.4 g) was recrystallized in absolute ethanol to yield 7.0 g of N-(3,3-diphenylpropionyl)-4-amino-4,8,8-trimethyl-1-azaadamantane tartrate (yield 80%).

Melting point: 224°–228° C. (ethanol).

EXAMPLES 7 TO 11

The process of Example 1 was repeated, replacing the propionic anhydride with benzoyl chloride or with p-methoxybenzoic acid chloride, and 4-N-benzoylamino-4,8,8-trimethyl-1-azaadamantane (Example 7) or N-(p-methoxybenzoyl)-4-amino 4,8,8-trimethyl-1-azaadamantane (Example 8), respectively, were obtained.

Likewise, using the process of Example 4, but replacing the 3-phenylpropionic acid with 2-phenylacetic acid or with 3,4-dimethoxyphenylacetic acid or with 4-phenylbutyric acid, N-phenylacetyl-4-amino-4,8,8-trimethyl-1-azaadamantane (Example 9), or N-(3',4'-dimethoxy-phenyl-acetyl)-4-amino-4,8,8-trimethyl-1-azaadamantane (Example 10), or N-(4-phenylbutyryl)-4-amino-4,8,8-trimethyl-1-azaadamantane (Example 11), respectively, were obtained, the characteristics of which are given in the following table.

| Example No. | MP (°C.) (Solvent) | I.R. Spectrum (cm$^{-1}$) (Nujol) | Salt | MP (°C.) |
|---|---|---|---|---|
| 7 | 130–132 (H$_2$O) | — | hydrochlor. | >260 |
| 8 | 110–120 (AcOEt) | 2500–3500,1630 1600,1555,1500 1245 | hydrochlor. | >260 |
| 9 | 169–171 (AcOEt) | 3300,1655,1635 1545,725 | tartrate | 100–110 |
| 10 | 169–171 (AcOEt) | 3290,1640,1610 1595,1545,1515 1265,1235,1160 1030,790 | hydrochlor. | >260 |
| 11 | 62–64 (AcOEt + | 3000–3500,1640 1565,1490,740 | hydrochlor. | >260 |

-continued

| Example No. | MP (°C.) (Solvent) | I.R. Spectrum (cm$^{-1}$) (Nujol) | Salt | MP (°C.) |
|---|---|---|---|---|
| | (i-C$_3$H$_7$)$_2$O) | 695 | | |

The 4-acylamino-1-azaadamantanes of the present invention have interesting toxicological and pharmacological properties, which demonstrate their use in human and veterinarian medicine.

Toxicological Study

The acute toxicity of the derivatives of the invention were studied by intraperitoneal administration (I.P.) on the mouse (10 animals, 5 males and 5 females per dose) and calculation of the lethal dose 50 (LD 50) in accordance with the method of Litchfield and Wilcoxon (*J. Pharmacol.* 96, 99–113 (1949)). Table 1 gives the LD 50 values for the derivatives whose preparation is described in Examples 1 to 11.

In certain cases (derivatives of Examples 4, 6, 9), the LD 50 was also calculated after oral administration (P.O.) of the derivatives.

TABLE 1

| LD 50 by Intraperitoneal and Oral Administration | | |
|---|---|---|
| Example No. | LD 50 I.P. (mg/kg) | LD 50 P.O. (mg/kg) |
| 3 | 95 | |
| 4 | 375 | 2400 |
| 5 | 250 | |
| 6 | 51 | 380 |
| 7 | 230 | |
| 8 | 250 | |
| 9 | 430 | 2400 |

Pharmacological Properties

A. Hemodynamic Tolerance

The hemodynamic tolerance of the derivatives of the invention was studied on dogs anesthesized with sodium pentobarbital. Endocavitary pressures were measured by means of catheters connected to Statham sensors while external recording of the electrocardiogram (E.C.G.) provided the measurement of cardiac frequency. Cardiac flow was measured by means of an electromagnetic sensor placed on the beginning of the aorta. The total peripheral resistances R were calculated from the value of the average aortic pressure ($\bar{P}$) and the cardiac flow (Q) in accordance with the formula $R = \bar{P}/Q$.

After measurement of the parameters during a control period, the derivatives were injected intravenously in cumulative doses (30 minute interval between doses). The variations of the parameters in relation to the control period were measured within 20 and 30 minutes after each injection and are expressed as a percentage of variation in relation to the control.

Table 2 summarizes the variations in hemodynamic parameters observed between the first and last injections.

TABLE 2

| | Cardiovascular Tolerance in the Anesthetized Dog (percentages of variation in relation to the control period) | | | | | |
|---|---|---|---|---|---|---|
| Example No. | Cumulative Doses mg/kg | Systolic Arterial Pressure | Cardiac Frequency | Cardiac Flow | dp/dt/p Left Ventricular | Total Peripheral Resistances |
| 3 | 0.1 to 3 | −3 to −33% | 0 to −14% | +7 to −32% | +14 to −50% | −10 to +7% |
| 4 | 0.3 to 10 | −7 to −28% | −7% | −7 to −23% | 0 to −40% | 0 to −13% |
| 5 | 1 to 10 | 0 to +3% | 0 | +4 to −8% | +2 to −15% | −6 to +11% |
| 6 | 0.1 to 1 | −8 to −16% | −3 to +10% | −3 to −18% | −6 to −13% | 0 |
| 8 | 0.3 to 10 | −6 to −21% | −7 to −15% | −7 to −22% | 0 to −28% | 0 |
| 9 | 1 to 10 | −5 to −28% | 0 to −12% | 0 to −30% | 0 to −33% | −5 to +15% |

These hemodynamic tolerance results show that:
Systolic arterial pressure decreases by 16 to 35% with all the derivatives except the derivative of Example 5 which produces no significant modification of this parameter (0 to +3%).
Cardiac frequency decreases moderately (maximum −15% with the derivative of Example 8) with the majority of the derivatives of the series except for the derivative of Example 5 where the frequency does not change and that of Example 6 where it increases slightly (+10%).
Cardiac flow is constantly decreased but these variations remain limited from −8 to −32%.
The ratio of the first differential quotient of the left ventricular pressure to the instantaneous left ventricular pressure decreases with strong doses by −13 to −50%.
The total peripheral resistances vary little.

In conclusion, cardiovascular tolerance in the anesthetized dog is satisfactory since the effects are limited to a moderate drop in cardiac flow, in contractility index and in systolic arterial pressure while the cardiac frequency and the total peripheral resistances vary diversely.

B. Experimental Atiarrhythmic Properties (a) Electrophysiological Studies on the Anesthetized Dog This study was carried out on dogs anesthetized with pentobarbital, with a closed thorax, by means of bipolar catheter-electrodes introduced into the cardiac cavities by transcutaneous venous and arterial means. The surface electrocardiogram (standard derivation D$_2$) is recorded permanently.

By means of a programmable JANSEN (R) stimulator, the following parameters may be measured:
spontaneous cardiac frequency (FC);
sinus recuperation time (SRT$_c$) after auricular stimulation imposed at 160 b/mn for 1 mn;
intracardiac conduction times (auriculohisien at a constant frequency, His-Purkinje, intraventricular);
the effective and functional refractory periods measured at an imposed constant frequency, with the extrastimulus method.

During the electrophysiological study, the derivatives were injected intravenously for 2 minutes for each dose and at 30 minute intervals between each dose. The doses are expressed as a cumulative value and as a base term.

The measurement of the various parameters was carried out before the injection of the first dose (control period) and from 10 to 28 minutes after the injection of each dose of the substance. The results are expressed as a percentage of variation in relation to the control period.

The electrophysiological effects of four examples of derivatives of the invention are given in Table 3.

The results obtained show that the derivatives of the invention have moderate (or inconstant) effects on sinusal automaticity whereas they produce a constant lengthening of the intracardiac conduction times at all levels, as well as a lengthening of the refractory periods. From these characteristics, the derivatives of the invention on the anesthetized dog produce effects typical of Group I of the Vaughan-Williams classification (the group of quinidine and its derivatives).

(b) Antiarrhythmic Tests

Antiarrhythmic activity was observed in the mouse by means of the Lawson test using the method described by J. W. Lawson, *J. Pharmacol. Exp. Ther.*, 160, 22–31, (1968) and C. Narcisse et al, *Ann. Pharma. Fr.*, 37, 325–330 (1979), in the rat by the aconitine intoxication test of S. Witchitz et al, *Coeur Med. Int.*, X(2), 281–286, (1971) and in the dog by the Harris test described in *Circulation*, 1, 1318, (1950) and by the test with adrenalin after experimental infarct of I. J. Steffe et al, *J. Pharmacol. Exp. Ther.*, 214, 50–57 (1980).

Aconitine Intoxication

The anesthetized rat was intoxicated with an intravenous perfusion of aconitine while its electrocardiogram (ECG) was permanently recorded. During the perfusion at constant rate, the time necessary for the appearance of ventricular arrhythmias, successive extrasystoles (ESV), then stable ventricular tachycardium (TV) and the time within which the animal died were measured.

The animals were divided into a control group (untreated) and treated groups (different doses). The results are expressed as a percentage of prolonging the time of appearance of the arrhythmias and of death of the treated groups in reaction to the control group.

The results obtained are shown in Table 4 below and express the percentage of prolongation of the time of appearance of ventricular arrhythmias (ventricular extrasystoles and ventricular tachycardiums), and of the death, induced by the aconitine after an intravenous injection (I.V.) of several derivatives of the invention, in relation to a group of untreated control animals.

TABLE 4

| Derivative No. | Injected Dose mg/kg | Ventricular Arrhythmias | | |
|---|---|---|---|---|
| | | ESV (%) | TV (%) | Death (%) |
| 8 | 5 | +45 | +43 | +46 |
| | 10 | +71 | +84 | +215 |
| | 20 | +98 | +107 | +112 |
| 6 | 1 | +52 | +93 | +69 |
| | 2 | +67 | +139 | +97 |
| 9 | 10 | +31 | +79 | +44 |
| | 20 | +100 | +79 | +84 |
| | 40 | +171 | +147 | +88 |
| 4 | 5 | +37 | +50 | +25 |
| | 10 | +60 | +86 | +39 |
| | 20 | +103 | +89 | +65 |
| 5 | 5 | +41 | +20 | +21 |
| | 10 | +51 | +48 | +36 |
| | 20 | +65 | +54 | +50 |
| 7 | 5 | +59 | +53 | +29 |
| | 10 | +35 | +35 | +45 |
| | 20 | +111 | +105 | +89 |

The results given in Table 4 show that the derivatives of the invention exert a protective effect against arrhythmias since they considerably prolong the time of appearance of ventricular arrhythmias and of death.

Lawson Test

The Lawson test is a test for the study of the cardiac antifibrillatory power of the derivatives. The mice (20 per group) received an intraperitoneal injection of the derivative 10 minutes before being placed in a chloroform-saturated atmosphere. Upon respiratory arrest, the thorax was opened (5 to 10 seconds) and whether or not the heart was in ventricular fibrillation was checked. The efficacy dose 50 (ED 50) of the derivative being studied is the dose which protects half the mice against anoxic ventricular fibrillation.

Table 5 summarizes the results of the Lawson test obtained with certain derivatives of the present invention.

TABLE 3

| Derivatives No. | No. of Evaluations | Doses (mg/kg) | Electrophysiological Effects VARIATION (%) | | | | | |
|---|---|---|---|---|---|---|---|---|
| | | | F.C. | St-H | HV | QRS | PREA | PREV |
| 3 | 3 | 0.5 to 5 | 0 to −24 | +2 to +76 | +13 to +98 | +8 to +39 | +2 to +50 | 0 to +20 |
| 4 | 2 | 0.3 to 14.3 | 0 | +7 to +10 | 0 to +80 | 0 to +15 | +10 to +35 | 0 to +10 |
| 6 | 1 | 0.1 to 1.4 | 0 to +32 | 0 to +25 | 0 to +92 | 0 to +50 | +18 to +50 | +10 to +20 |
| 9 | 2 | 1 to 19 | 0 | 0 to +30 | +18 to +100 | 0 to +23 | +6 to +45 | +2 to +15 |

F.C.: Cardiac frequency
St-H: Time of auriculo-hisien conduction
HV: Time of His-Purkinje conduction
QRS: Time of intraventricular conduction
PREA: Effective auricular refractory period
PREV: Effective ventricular refractory period

TABLE 5

| Derivative No. | ED 50 (mg/kg) | Maximum Dose Tolerated (mg/kg) |
|---|---|---|
| 3 | 37 | 50 |
| 4 | 72 | 200 |
| 5 | 61 | 200 |
| 7 | 76 | 150 |
| 8 | 49 | 100 |
| 9 | 90 | 200 |

These results show that the derivatives of the invention possess satisfactory antifibrillatory activity, comparable to that of a known compound such as quinidine.

Harris Test

The ligature of the anterior interventricular artery in the anesthetized dog causes the appearance of an experimental infarct of the myocardium followed by considerable ventricular arrhythmias.

The dogs were studied 24 to 48 hours after the intervention. The electrocardiogram (ECG) was then recorded permanently, the conscious dog being at rest in an isolated laboratory. After a period of 3 hours of ECG recording, allowing for the measurement of the cardiac frequency of the dog the frequency of ventricular extrasystoles (ESV)—pre-treatment control period—the derivative to be studied was injected intravenously for 1 minute. Continuous recording of the ECG enabled, in the hours following the injection, measurement of the frequency of the ESV/mn for successive periods from 30 to 60 min. The number of ESV per minute measured for 3 hours during the control period varied from 66 to 172/min with an average of 111/min. It was noticed that the derivatives of the invention caused a considerable decrease in the number of ESV per minute, on the order of 35% to 95% depending upon the derivative and the dose administered (1 to 14 mg/kg). The length of this antiarrhythmic effect observed varied depending on the derivatives from 1 hour to more than 5 hours. For example, the percentage decrease of the ESV/min in the case of the derivative of Example 11 (cumulative dose 14 mg/kg) was 96% (0 to ½ hour), 50% (½ to 1 hour) and 68% (1 to 2 hour). The corresponding values for the derivative of Example 4 (3 mg/kg) were 44%, 55% and 45%, respectively.

Ventricular Arrhythmias with Adrenalin after Experimental Infarct 2 to 5 days after an experimental infarct, the effects of discontinuous injections (in intravenous bolus of 4 g/kg of basic adrenalin) of adrenalin were observed on the electrocardioagram of the conscious dog.

During a first phase (control) of the experiment, three successive injections of adrenalin were given and, in the 2 minutes following each injection, the frequency of the ventricular extrasystoles was measured. In this manner, by increasing the dose of adrenalin as necessary, it was possible to determine the dose which caused the appearance of ventricular extrasystoles at a higher frequency than or equal to half the total number of ventricular systoles.

After injection of the derivative to be tested, the same dose of adrenalin was reinjected after 5 minutes, then 30 minutes, 60 minutes, 90 minutes, etc., and its effects were compared to those observed during the control period.

Table 6 summarizes the results obtained with the adrenalin test. The results therein are expressed as a percentage of extrasystoles (on the total number of systoles) measured during the 2 minutes following the injection of adrenalin before and after the administration of the derivative to be tested. The results in this table show that the antiarrhythmic effects can be maintained for more than one hour and can continue until the almost total disappearance of the arrhythmias caused by the adrenalin.

TABLE 6

| | Test with Adrenalin after Experimental Infarct | | | | |
|---|---|---|---|---|---|
| Example No. | Control Period (% of ESV) | Injected Dose (mg/kg) | ESV Percentage at | | |
| | | | 5 min | 30 min | 60 min |
| 3 | 94% | 4.3 | 63% | 77% | 90% |
| 4 | 74% | 14.3 | 36% | 59% | 60% |
| 5 | 40% | 10 | 9% | 14% | 16% |
| 6 | 85% | 1.3 | 29% | 17% | 17% |
| 8 | 71% | 4 | 35% | 36% | 53% |
| 9 | 48% | 1 | 11% | 27% | 45% |

It can therefore be noted that the derivatives of the 4-acylamino 1-azaadamantane type of the present invention possess important antiarrhythmic properties on various experimental models, whether intoxication with aconitine or acute myocardiac ischaemia. Their cardiovascular tolerance is good since negative hemodynamic effects remain limited. A study of their electrophysiological cardiac properties shows that these derivatives possess "quinidine-like" characteristics of Group I of antiarrhythmics, and that they act well at both the supraventricular and ventricular levels, which enables extended antiarrhythmic potentiality.

These properties show that the derivatives of the invention can be used in human and veterinarian medicine, in particular for the treatment of cardiovascular diseases, and more particularly for the treatments of various forms of cardiac arrhythmias, both supraventricular and ventricular.

The derivatives of the 4-acylamino-1-azaadamantane type of the invention and their pharmaceutically acceptable salts can be administered in conventional forms, the active constituent being employed with an appropriately selected pharmaceutically acceptable carrier, for example, in the form of tablets, capsules, lozenges, suppositories, injectable solutions or syrups.

By way of example, tablets can be prepared by mixing the derivative of general formula (I) or one of its salts with one or several solid diluents such as lactose, mannitol, starch, polyvinylpyrrolidone, magnesium stearate, talc, etc. Where necessary, the tablets may comprise several layers superposed around a nucleus, in accordance with conventional techniques, in order to ensure progressive liberation or a delayed effect of the active ingredient. The coating may, for example, be composed of one or several layers of polyvinyl acetate, carboxymethylcellulose or cellulose acetophthalate.

The derivative of the invention may also be administered in the form of a syrup or drinkable solution obtained by dissolving the derivative of formula (I) or one of its pharmaceutically acceptable salts, in water or glycerol, for example, and adding as necessary a conventional additive such as a sweetener and an antioxidant.

Injectable solutions can be prepared using well-known techniques and can be composed, for example, of a solution containing a derivative of formula (I) or one of its pharmaceutically acceptable salts, dissolved in bidistilled water, a hydroalcoholic solution, propyleneglycol, etc., or a mixture of such solvents. Where necessary, an appropriate additive such as a preservative may be added.

Dosages may vary in accordance with the type of condition and the subject being treated. Doses administered daily are generally comparable to those of quinidinic treatments, (e.g. 5 to 50 mg-leg[31] [1] orally) but can

What is claimed is:

1. A 4-acylamino-1-azaadamantane represented by the general formula (I):

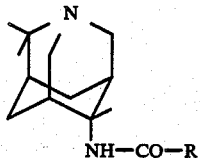

wherein R is an usubstituted aryl group selected from the group consisting of phenyl, benzyl, phenethyl, phenylpropyl, diphenylethyl and diphenylpropyl or said aryl group is substituted by one or two of a halogen atom, an alkyl of 1 to 4 carbon atoms, hydroxy, methylenedioxy, alkoxy of 1 to 3 carbon atoms, amino, alkylamino having 1 to 3 carbon atoms in the alkyl moiety, dialkylamino having 1 to 3 carbon atoms in the alkyl moiety, nitro, cyano, acetylamino, alkanoyl of 1 to 4 carbon atoms, trifluoromethyl or trichloromethyl group, or a pharmaceutically acceptable acid salt thereof.

2. The 4-acylamino-1-azaadamantane of claim 1, wherein R represents a phenyl, benzyl, phenethyl, phenylpropyl, 2,2-diphenylethyl, 3,3-diphenylpropyl, p-nitrophenyl, p-aminophenyl, p-acetylaminophenyl, p-methoxyphenyl, 3,4-dimethoxyphenyl, 3,4-dimethoxybenzyl, p-methoxybenzyl, p-methoxyphenethyl or 3,4-methylenedioxy-phenyl group.

3. The 4-acylamino-1-azaadamantane of claim 1 in the form of the pharmaceutically acid salt thereof.

4. The 4-acylamino-1-azaadamantane of claim 2 in the form of the pharmaceutically acid salt thereof.

5. The 4-acylamino-1-azaadamantane of claim 2 in the free form thereof.

6. The 4-acylamino-1-azaadamantane of claim 1 in the free form thereof.

7. A 4-acylamino-1-azaadamantane represented by general formula (I):

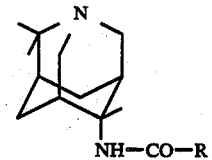

wherein R is an unsubstituted aryl group selected from the group consisting of phenyl, benzyl, phenethyl, phenylpropyl, diphenylethyl and diphenylpropyl or said aryl group substituted by one or two of a halogen atom or an alkyl of 1 to 4 carbon atoms, hydroxy, methylenedioxy, alkoxy of 1 to 3 carbon atoms, amino, nitro, cyano, acetylamino or lower alkanoyl of 1 to 4 carbon atoms or a pharmaceutically acceptable acid salt thereof.

8. A pharmaceutical composition for treating cardiac arrhythmias comprising a therapeutically effective amount of a 4-acylamino-1-azaadamantane or a pharmaceutically acceptable acid salt thereof of claim 1, as an active ingredient, and a pharmaceutically acceptable carrier or diluent.

9. A pharmaceutical composition for treating cardiac arrhythmias comprising a therapeutically effective amount of a 4-acylamino-1-azaadamantane or a pharmaceutically acceptable acid salt thereof of claim 2, as an active ingredient, and a pharmaceutically acceptable carrier or diluent.

10. A pharmaceutical composition for treating cardiac arrhythmias comprising a therapeutically effective amount of a 4-acylamino-1-azaadamantane or a pharmaceutically acceptable acid salt thereof of claim 3, as an active ingredient, and a pharmaceutically acceptable carrier or diluent.